(12) United States Patent
Lubowski

(10) Patent No.: US 6,350,233 B1
(45) Date of Patent: Feb. 26, 2002

(54) SIGMOIDOSCOPE

(76) Inventor: David Z. Lubowski, 4 Cranbrook Road, Rose Bay, New South Wales 2029 (AU)

( * ) Notice: Subject to any disclaimer, the term of this patent is extended or adjusted under 35 U.S.C. 154(b) by 0 days.

(21) Appl. No.: 09/363,773

(22) Filed: Jul. 29, 1999

(30) Foreign Application Priority Data

Jul. 30, 1998 (AU) .............................................. PP 4960
Oct. 29, 1998 (AU) .............................................. PP 6801

(51) Int. Cl.⁷ .................................................. A61B 1/12
(52) U.S. Cl. ....................... 600/158; 600/159; 600/133; 600/135; 604/37; 604/110; 604/517
(58) Field of Search ................................ 600/159, 158, 600/156, 133, 135; 604/28, 36, 37, 110, 517

(56) References Cited

U.S. PATENT DOCUMENTS

| | | | |
|---|---|---|---|
| 3,709,214 A | * | 1/1973 | Robertson ........................ 128/4 |
| 3,779,233 A | * | 12/1973 | Saslow et al. .................. 128/6 |
| 3,889,661 A | * | 6/1975 | Fiore ............................. 128/6 |
| 4,852,551 A | * | 8/1989 | Opie et al. ..................... 128/4 |
| 4,869,238 A | * | 9/1989 | Opie et al. ..................... 128/6 |
| 5,518,501 A | * | 5/1996 | Oneda et al. ................ 600/127 |
| 5,692,729 A | * | 12/1997 | Harhen ........................... 251/4 |
| 5,725,478 A | * | 3/1998 | Saad ........................... 600/157 |
| 5,931,833 A | * | 8/1999 | Silverstein .................... 606/1 |

* cited by examiner

Primary Examiner—Linda C. M. Dvorak
Assistant Examiner—Jocelyn Ram
(74) Attorney, Agent, or Firm—Dorsey & Whitney LLP

(57) ABSTRACT

A sigmoidoscope comprising at least one disposable part (1), in combination with means (10) for insufflation of a body cavity with a medium via the sigmoidoscope; said medium being susceptible to contamination by a contaminant (as herein defined) during use of the sigmoidoscope, said insufflation means (10) and said sigmoidoscope (eg part 1) being connected, or adapted for connections one to the other; the sigmoidoscope and/or the insufflation means being provided with disposable contamination prevention means (18), or being so formed and arranged, that no non-disposable part of the sigmoidoscope (eg 15) and no non-disposable part of the insufflation means is exposed to any contaminated medium during use of the sigmoidoscope.

18 Claims, 12 Drawing Sheets

SIGMOIDOSCOPE

FIELD OF THE INVENTION

This invention relates to a sigmoidoscope for use in examination of the bowel or other body cavity and to sigmoidoscopy.

BACKGROUND ART

It is frequently necessary for a medical practitioner to inspect the colon or rectum of a patient. This procedure is commonly conducted with a sigmoidoscope which in the past consisted of a metal tube or speculum adapted at one end for insertion into the rectum of a patient and adapted at the other end for connection with a manifold. The manifold was provided with an observation window, a rubber bulb insufflator connectable via a spigot to the manifold and communicating with the interior of the speculum whereby the bowel may be pressurised, and an illuminator with which at least a portion of the bowel interior may be illuminated during examination. In the past, after use and before reuse on a subsequent patient, the metal tube was sterilised. Subsequently there were developed sigmoidoscopes in which parts coming in contact with the patient were designed to be thrown away after use to save the time and expense of cleaning and sterilising.

Presently used sigmoidoscopes employ a disposable speculum in the form of a hollow, light transmissive, plastic tube. The disposable speculum is purchased in a clean or sterile condition sealed in a bag together with a disposable obturator adapted for use with the speculum. In use the disposable speculum is coupled to a non-disposable fibre optic head which has a hinged window through which an obturator or biopsy instrument may be inserted and removed coaxially through the interior of the speculum.

A light source is operatively coupled with the speculum via the fibre optic head so as to illuminate a circumferential end edge of the speculum via fibre optics whereby light from the illumination means may be directed through the wall of the speculum into the anal canal, bowel, or other body cavity under examination. The fibre optic head is also provided with a spigot for connection, for example via a flexible communicating tube, to an insufflation bulb with which the bowel may be insufflated with air. After use the obturator is discarded.

Upon conclusion of an examination the inexpensive plastic disposable speculum is also disconnected from the fibre optic head and disposed of The fibre optic head together with the hinged window mounted thereto and, fibre optic illumination means costs in excess of $750 and are retained for use with another speculum. The insufflation bulb may be disconnected between uses but commonly remains connected to the fibre optic head.

Although the invention will be herein described with reference to sigmoidoscopy, it will be understood that the invention is equally applicable to other forms of endoscopy which involve inflation of an internal cavity to be examined and is not limited to instruments for use in bowel examination.

The present inventor has discovered a previously unrecognised potential for cross-infection from sigmoidoscopy.

OBJECT OF THE INVENTION

It is an object of the present invention to provide an improved sigmoidoscope and an improved method for conducting sigmoidoscopy which avoids or ameliorates a disadvantage of the prior art.

BRIEF DESCRIPTION OF THE INVENTION

According to one aspect the invention consists of a sigmoidoscope comprising at least one disposable part, in combination with means for insufflation of a body cavity with a medium via the sigmoidoscope; said medium being susceptible to contamination by a contaminant (as herein defined) during use of the sigmoidoscope; said insufflation means and said sigmoidoscope being connected, or adapted for connection, one to the other; the sigmoidoscope and/or the insufflation means being provided with disposable contamination prevention means or being so formed and arranged that no non-disposable part of the sigmoidoscope and no non-disposable part of the insufflation means is exposed to any contaminated medium during use of the sigmoidoscope.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

The sigmoidoscope may be an assembly including a plurality of disposable parts, for example a disposable speculum and a disposable eyepiece and may include one or more non-disposable components, for example an illuminator. The means for insufflation is commonly an inflation bulb together with a flexible hollow tube whereby the bulb communicates with the sigmoidoscope and in such case the insufflation medium is air.

A "contaminant" as herein defined is any agent capable of infection and includes, without limitation, viruses, bacteria, fungii, protozoa, mycoplasma and organic or inorganic carriers of any of the above.

According to a second aspect the invention consists in a sigmoidoscope disposable part having means for connection to a reusable insufflation means and wherein the disposable part or the insufflation means includes disposable contamination prevention means for preventing contamination of the reusable insufflation means during sigmoidoscopy.

The disposable part may for example be a disposable speculum. Contamination prevention means may, for example, be a non-return valve, a filter such as a nanopore filter, an electrostatic precipitator or other means which prevent internal surfaces of the reusable insufflation means from becoming contaminated by, for example, contaminants which become airborne during a sigmoidoscopy procedure and transferred from the patient to the sigmoidoscope interior, or are transferred for example by wall contact of an instrument. It will be understood that the term "insufflation means" includes any tubing communicating between an insufflation bulb or other source of insufflation medium and the sigmoidoscope.

According to a third aspect the invention consists in a sigmoidoscope disposable part having insufflation means permanently connected therewith for disposal with the disposable part. Preferably the disposable part is a speculum.

According to a fourth aspect the invention consists in a method for preventing cross-contamination from a first patient to a second patient during sigmoidoscopy said method comprising the steps of (1) Examining a body cavity of the first patient by means of a sigmoidoscope used in combination with insufflation means for introducing an insufflation medium to the body cavity, and (2) Prior to examining the second patient, disposing of all parts of the sigmoidoscope and of the insufflation means which have been exposed to contaminants in the insufflation medium.

Other aspects of the invention relate to a disposable obturator.

It has hitherto been assumed that disposal of the speculum and obturator after each use suffices to avoid cross-contamination. The possibility of cross-contamination via the insufflation medium and internal surfaces of the non-disposable insufflation bulb has not previously been considered. In addition, with many current sigmoidoscope designs, there is communication between portions of the internal surface of the fibre optic bead or of the observation window and surrounding eyepiece which are exposed to the insufflation medium. The present inventor considered that there may be a potential for microorganisms to be passed from one patient to another and carried out tests as hereinafter described to examine the possibility of bacteria contaminating the inside surface of an insufflation bulb and connecting tubing and/or non-disposable fibre optic light head and thereby the potential for cross-contamination. The results have surprisingly revealed that there is a potential for cross-contamination during sigmoidoscopy. The present invention provides a modified apparatus and method whereby this previously unsuspected potential for cross-contamination can be avoided.

BEST MODE FOR CARRYING OUT THE INVENTION

Figure 1:
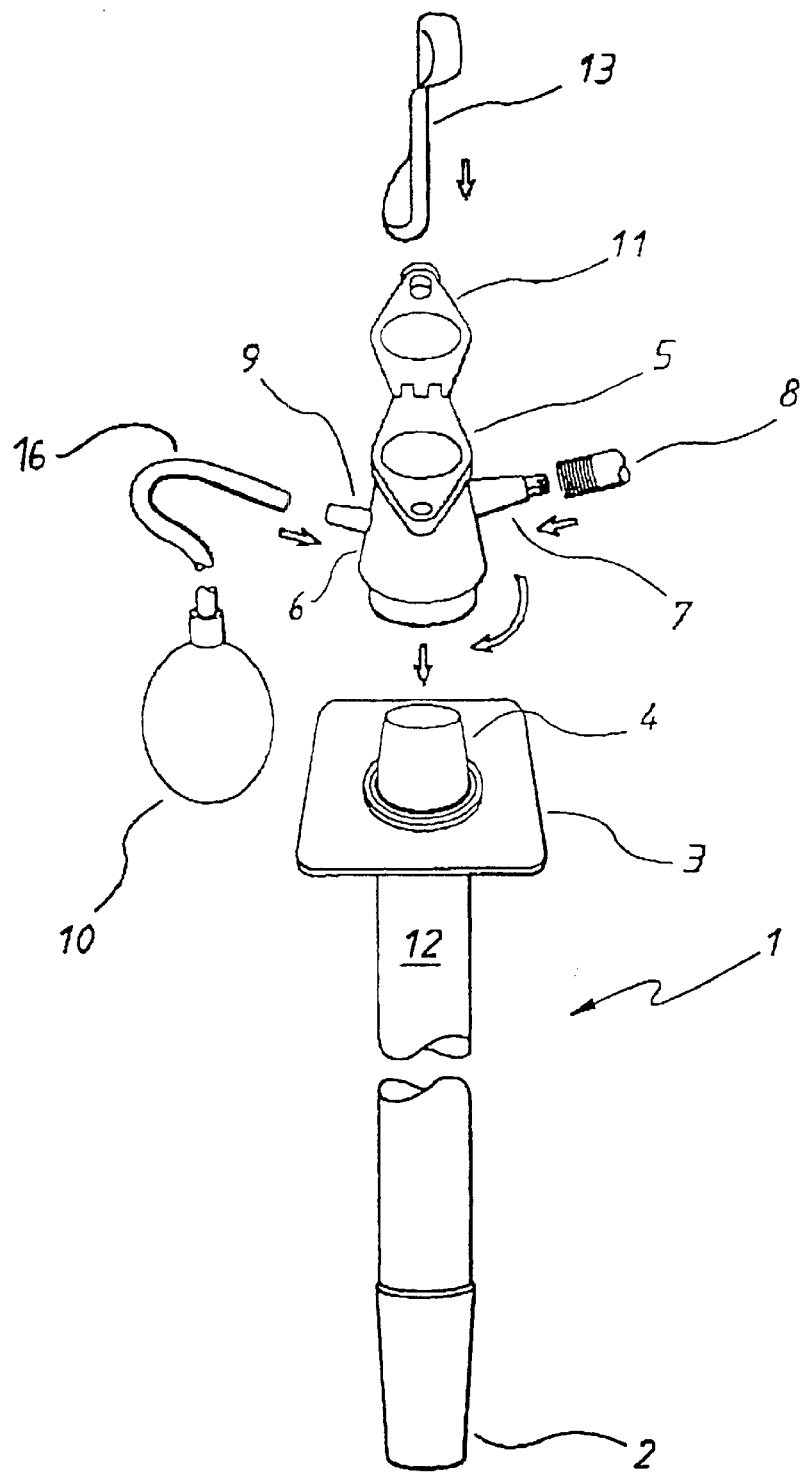
FIG. 1 is a general exploded view of a sigmoidoscope according to the prior art.

An example of a prior art sigmoidoscope commonly used for the examination of a patient's bowel is shown in FIG. 1. The instrument includes a disposable speculum 1 which consists of a hollow plastic tube having good light transmission properties. An insertion end 2 is adapted to be inserted into a patient's anal canal with a minimum of discomfort. An obturator 13 is adapted to pass axially through the interior of speculum 1 and aids in insertion of end 2 of the speculum into a patient. An integral shield 3 is provided adjacent the observation end 4 to prevent other, non-disposable, parts from coming into contact with the patient. Observation end 4 is adapted to releasably engage a fibre optic head 5 those parts being coupled, for example, by a bayonet connection or screw threaded engagement.

Fibre optic head 5 constitutes coupling means for optically coupling a light source 8 with the speculum. Fibre optic head 5 includes a hollow body 6, adapted to sleeve over speculum end 4 such that by looking through body 6 in the speculum axial direction when head 5 is coupled to speculum 1 an unobstructed view path is provided through the speculum to the insertion end 2. Fibre optic head 5 further includes means 7 for the releasable attachment of a light source 8. Fibre optic head 5 also has a hollow spigot 9 for the releasable attachment of a squeeze bulb 10 or other insufflation means via a flexible tube 16. Spigot 9 communicates with the interior of body 6 whereby the interior of speculum 1 may be pressurised in use with an insufflation medium, in this case air. A window 11 is hingedly mounted to head 5. When hinged open, window 11 allows passage of obturator 13. When in a closed position window 11 may be securely and fluid-tightly sealed to head 5. Window 11 when closed, in combination with the interior of speculum 1, defines a pressurisable "chamber" or interior 12 whereby to allow the insufflation of a patients bowel.

In use of the prior art sigmoidoscope of FIG. 1, a clean or sterile speculum 1 and obturator 13 are removed from their packaging. Obturator 13 is slidingly inserted from the observation end as far as it will go into speculum 1. The obturator extends out of the insertion end 2 of speculum 1 and closes that end to aid in anal insertion of the speculum. After insertion of the speculum obturator 13 is withdrawn and discarded. Fibre optic head 5 is then coupled to the observation end 4 of speculum 1, for example via a bayonet fitting or threaded engagement. Hinged window 11 is secured in the closed position. Insufflation means, in this example, a squeeze bulb 10 and including connection tube 16, is then attached to the sigmoidoscope by connection of the free end of tube 16 to spigot 9 of head 5. The patients bowel is insufflated to allow the physician to more easily observe the condition of the bowel. Before or after insufflation electric light source 8 is connected to attachment means 7 of fibre optic head 5 and is energised. Light travels from source 8 through the fibre optic head and then along speculum 1 to its insertion end 2 where it is emitted from the tube and illuminates the patients bowel at least in the region observable by a physician looking Through hinged window 11. After use speculum 1 is removed and bead 5 detached. Disposable speculum 1 is then discarded whilst head 5 including hinged window 11, light source 8, and bulb 10 with tube 16, which have not come into direct contact with the patient, are retained for use with a new speculum 1 on another patient. It will be understood that some physicians may assemble or disassemble the sigmoidoscope parts in a different order and in the prior art may connect or disconnect the insufflation means 10, 16 at any stage of the assembly or disassembly or may leave the insufflation means connected with head 5.

It has hitherto been assumed that disposal of the speculum and obturator suffices to avoid cross-contamination. It has also been assumed that because the light source is isolated from the sigmoidoscope interior by a fibre optic coupling and the interior of the coupling is sleeved over the observation end of the disposable speculum there will be no contamination of non-disposable parts. The possibility of cross-contamination via the non-disposable bulb 10 or connection tube 16 has not previously been considered. Although sigmoidoscopy is a widely practised procedure the present inventor has found no record of bacterial or cross-contamination during sigmoidoscopy being formally investigated. In addition there is a possibility with current sigmoidoscope designs that there is communication between portions of the internal surface of fibre optic head 5 exposed to the insufflation medium, the internal surface of window 11 and the surrounding eyepiece on the one hand; and the lumen of a rectum on the other. The present inventor considered that there may be a potential for microorganisms or other contaminants to be passed from one patient to another and carried out tests to examine the possibility of bacteria contaminating the inside surface of the inflation bulb and connecting tubing and thereby the hitherto unsuspected potential for cross-contamination.

METHOD OF DETERMINING CONTAMINATION

Twenty-one patients undergoing rigid sigmoidoscopy as part of their clinical assessment were entered into the study. In the first 12 subjects the non-disposable bellows and tubing of the Welch Allyn disposable sigmoidoscope set was replaced with a sterile Jackson-Pratt bulb. This bulb is usually used as a closed wound suction drainage system. The egg-shaped bulb has an inlet port with an anti-reflux valve, and a drainage port with removable plug, and is supplied in a sterile plastic pack.

The patient was placed in the left lateral position on the examination bed for sigmoidoscopy. The Jackson-Pratt bulb (Baxter Healthcare, Deerfield, Ill., USA) was removed from its container using aseptic technique. The drainage port was connected to a length of sterile connection tubing, which in turn was connected to the non-disposable Welch Allyn sigmoidoscope light head. Sigmoidoscopy was carried out using a disposable sigmoidoscope (Welch Allyn, N.Y.). No biopsies were taken. In the first 6 of these 12 patients the light head was washed and then sterilised in the autoclave at 120° C. under pressure for 15 minutes before each case.

At the completion of the sigmoidoscopy the instrument was withdrawn, and using aseptic technique the bulb was disconnected from the tubing and instilled with 20 ml sterile saline via the drainage port. The plug was then inserted into the drainage port and the saline was gently swirled in the bulb. A sterile steri-strip tape was placed to seal the inlet port. The bulb was then sent to the pathology laboratory for microbiological examination of the contents of the saline. Cultures were set up on Blood Agar, MacConkay Agar and Chocolate Agar for gram positive and gram negative aerobic and anaerobic organisms, and on LJ Slope for mycobacteria. Incubation was continued for 48 hours, and once a growth was found it was maintained longer for organism identification.

Test were carried out on the sigmoidoscope light head in a further 9 patients. For this part of the study the light head was washed and sterilised at the beginning of each consulting session and then used on several consecutive patients. In each case the sigmoidoscope was inserted, the obturator withdrawn, and the light head then connected to the sigmoidoscope. At the end of the examination new gloves were used and swabs were taken from the inside surface of the light head and eyepiece. The swabs were placed in Amies transport medium and subsequently plated on Blood Agar, Chocolate Agar, and Colistin/Naladixic Acid Blood Agar.

RESULTS

Cultures from the Jackson-Pratt bulbs identified no organisms in 9 of the 12 cases. In three cases the following cultures were found: 1) 100–1000 colonies/ml *E. coli* and mixed anaerobic organisms; 2) 100–10 000 colonies *E. coli* and mixed anaerobic organisms; 3) a small count (<10 colonies/ml) Staph. Epidermidis. The first of these three cases was in the group in which the light head had been sterlised immediately before use.

Cultures from the light heads showed no growth in 7 of 9 cases. In two cases the following organisms were found: 1) one colony of Bacillus species; 2) *Proteus mirabilis, Klebsiella pneumoniae*, and *Enterococcus faecalis*.

DISCUSSION OF RESULTS

These results show that there is a hitherto unsuspected potential for cross-contamination of patients when using the commercially available prior art apparatus according to conventional procedures. This is thought to arise from bacteria or fluid droplets containing contaminants which may be entrained with the insufflation medium and which may contaminate interior surfaces of the coupling head or inflation bulb which are exposed to the medium during examination. Although no tests have been conducted for passage of viable organisms from one patient to another, it is apparent from the results obtained that there is a substantial risk of cross-contamination if such parts as the insufflation bulb and non-disposable eyepiece are reused without sterilisation. In addition currently used sigmoidoscopes permit contamination of the interior surface of the coupling means and/or window during retraction of the obturator and/or of a biopsy sampling device.

PREFERRED EMBODIMENTS OF THE INVENTION

Figure 2:
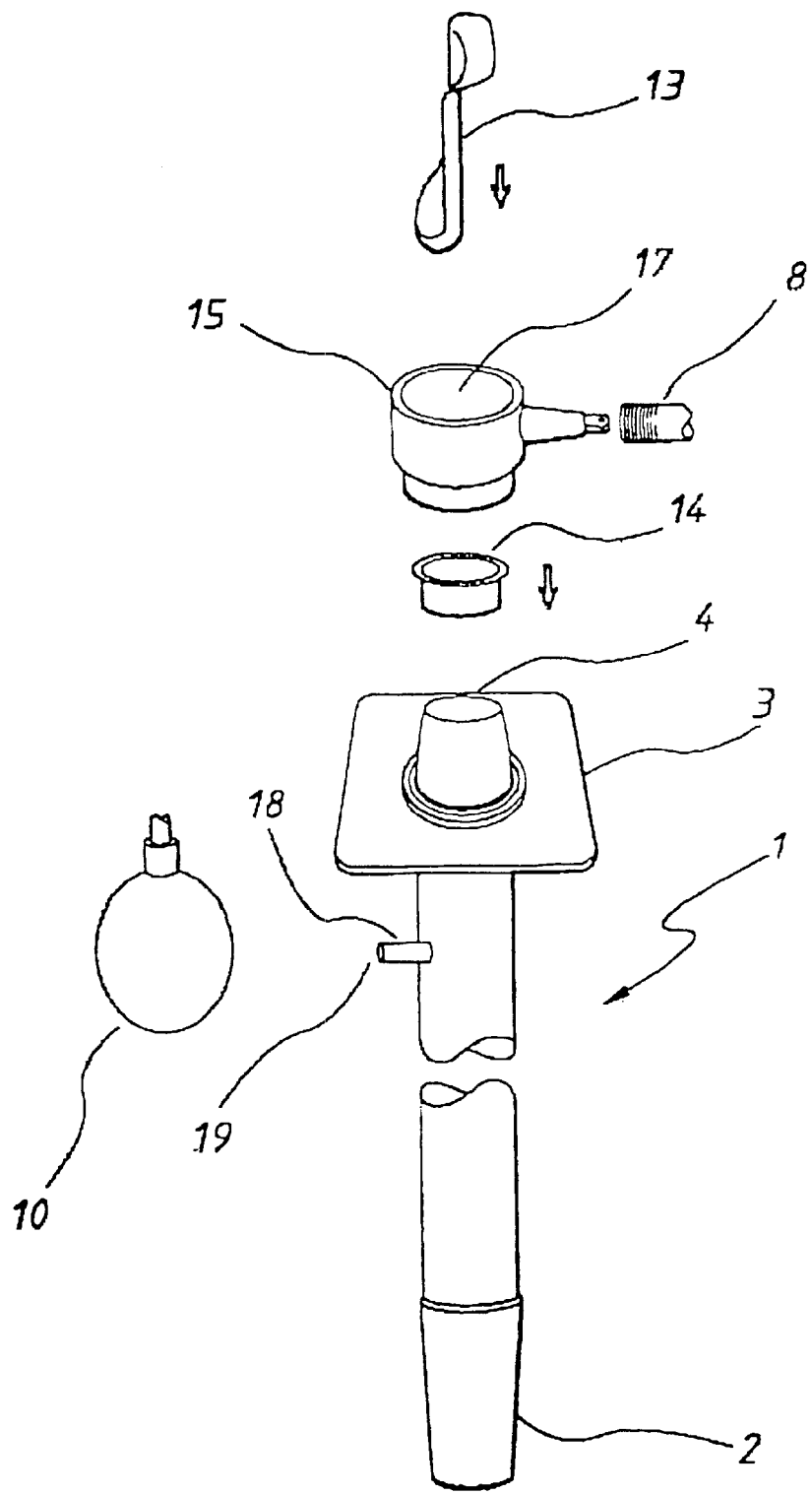
FIG. 2 is a general exploded view of a first embodiment of a sigmoidoscope according to the invention for use with a non-disposable insufflation bulb.

With reference to FIG. 2, there is illustrated a first embodiment of a sigmoidoscope according to the invention of which a part is a disposable speculum 1 having a insertion end 2 and a observation end 4. The disposable speculum 1 differs from that of the prior art apparatus of FIG. 1 in that there is provided, adjacent the observation end, an inlet port 19 in the form of a hollow spigot whereby the hollow interior of speculum 1 is adapted for the releasable attachment of a non-disposable squeeze bulb 10 or other insufflation means to the external side of inlet port 19. Desirably the spigot of inlet port 19 is barbed to facilitate connection of flexible tubing. Speculum 1 is provided with contamination prevention means whereby a contaminant if any carried by the insufflation medium from a patients body is prevented from contacting an interior surface of the non-disposable insufflation bulb 10 or to prevent the contaminant from entering a tube 16 communicating between bulb 10 and port 19. The contamination prevention means 18 may, for example, be a one-way valve disposed between the interior of speculum 1 and the exterior of port 19, or maybe a suitable air permeable filter, for example a microporous membrane filter extending across port 19 and effective to prevent passage of contaminants or may, for example, be a baffled passageway providing an air path of sufficient tortuosity. To prevent airborne contaminants emanating from the bowel lumen from contact with the interior of bulb 10 or of tubing 16. Contamination prevention means 18 are disposed of along with speculum 1.

By "disposable" is herein meant that a part or component is intended to be discarded after a single use. Disposable items are normally made of a relatively inexpensive material and are of a cost such that the cost of replacement of the item is comparable to the cost of cleaning and sterilising, or is an acceptably low cost in comparison having regard to the risks arising from non-disposal. Those of ordinary skill in the art will generally have no difficulty in recognising whether or not an article is intended for disposal.

The sigmoidoscope assembly of FIG. 2 further differs from that of FIG. 1 in that a disposable fluid tight window 14, attachable to speculum 1 at or adjacent to the observation end 4 is provided. Disposable window 14 in combination with the interior of speculum 1 defines a fluid tight chamber 12. Window 14 may be part of an eyepiece adapted to be inserted into observation end 4 and retained in place by a friction fit.

Figure 3:
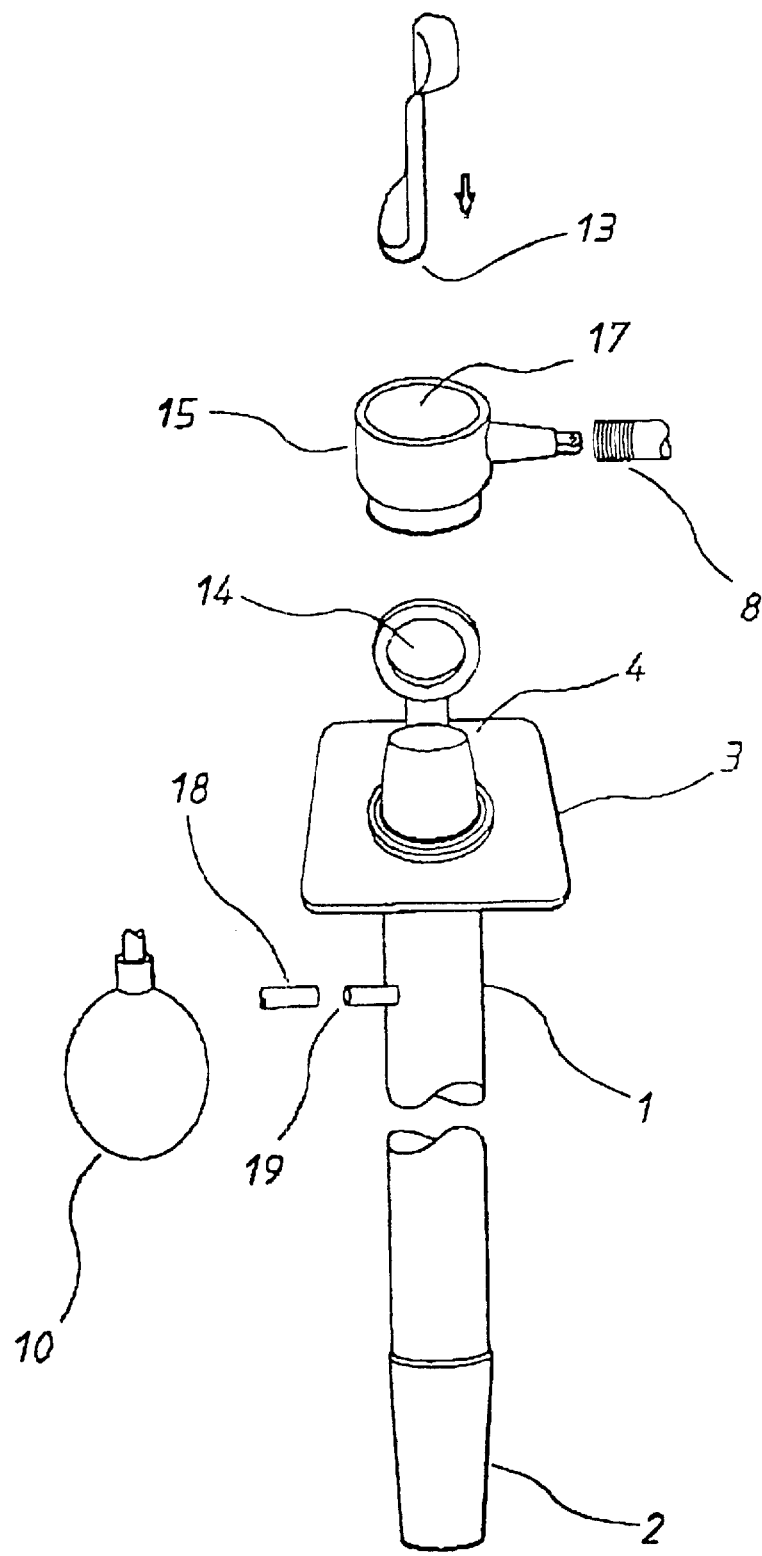
FIG. 3 is a general exploded view of a second embodiment of a sigmoidoscope according to the invention.

Alternatively as shown in FIG. 3, disposable window 14 may be hingedly connected with disposable speculum 1. In use obturator 13 is slidingly inserted as far as it will go into speculum 1. At this point the obturator extends out of the speculum insertion end 2 and closes that end to aid in the insertion of the speculum. After insertion obturator 13 is withdrawn and disposed of. Fluid tight window 14 is then inserted at the observation end of speculum. Coupling means 15 are then attached at or adjacent to observation end 4 of speculum 1, substantially overlaying window 14 A reusable squeeze bulb 10 is then attached to inlet port 19 and the patients bowel insufflated. A light source 8 is attached to coupling means 15 and is activated. Light travels through coupling means 15 and then along speculum 1 to its insertion end 2 at which point it exits the tube and then illuminates the patients bowel at least in the region observable by a physician looking through the viewing port 17 of the coupling means. After use speculum I is removed and coupling means 15 and squeeze bulb 10 are detached. Contamination prevention means 18 (one-way valve, filter or the like) in the embodiment of FIGS. 2 and 3 prevents contamination of retained squeeze bulb 10 and connecting tube 16, if any. Disposable speculum 1 including contamination prevention means 18 and disposable window 14 are then discarded whilst the other components of assembly, of which none have come into direct contact with the patient or been exposed to contamination, are retained for use with a new speculum 1 on a new patient.

Figure 4:
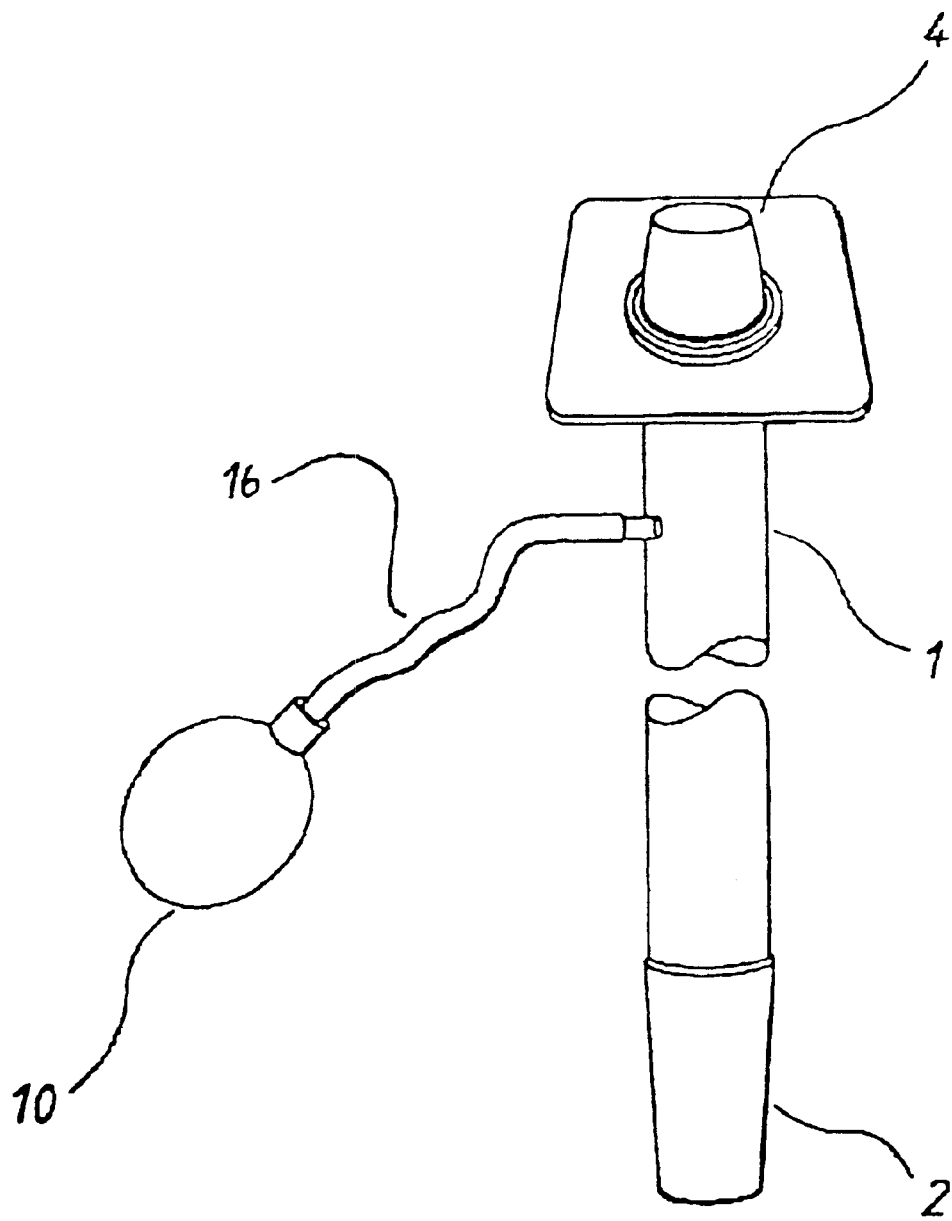
FIG. 4 shows an embodiment of a speculum for use in the sigmoidoscope of FIG. 2 or FIG. 3 and having an integral disposable insufflation bulb.

In a second embodiment of the invention shown in FIG. 4, a disposable bulb 10 is integrally attached to port 19 and is disposed of, after a single use, along with speculum 1. For example, bulb 10 may be moulded integrally with or welded or adhered to tube 16 which in turn is welded or adhered to port 19. In embodiments of the invention where a disposable squeeze bulb 10 is used contamination prevention means 18 need not be provided intermediate the speculum interior and squeeze bulb 10. Desirably, in this case, the bulb is so formed and arranged that it is permanently attached to speculum 1 to ensure that the combined speculum 1, bulb 10 and connecting tube 16 are disposed of together.

Figure 5:
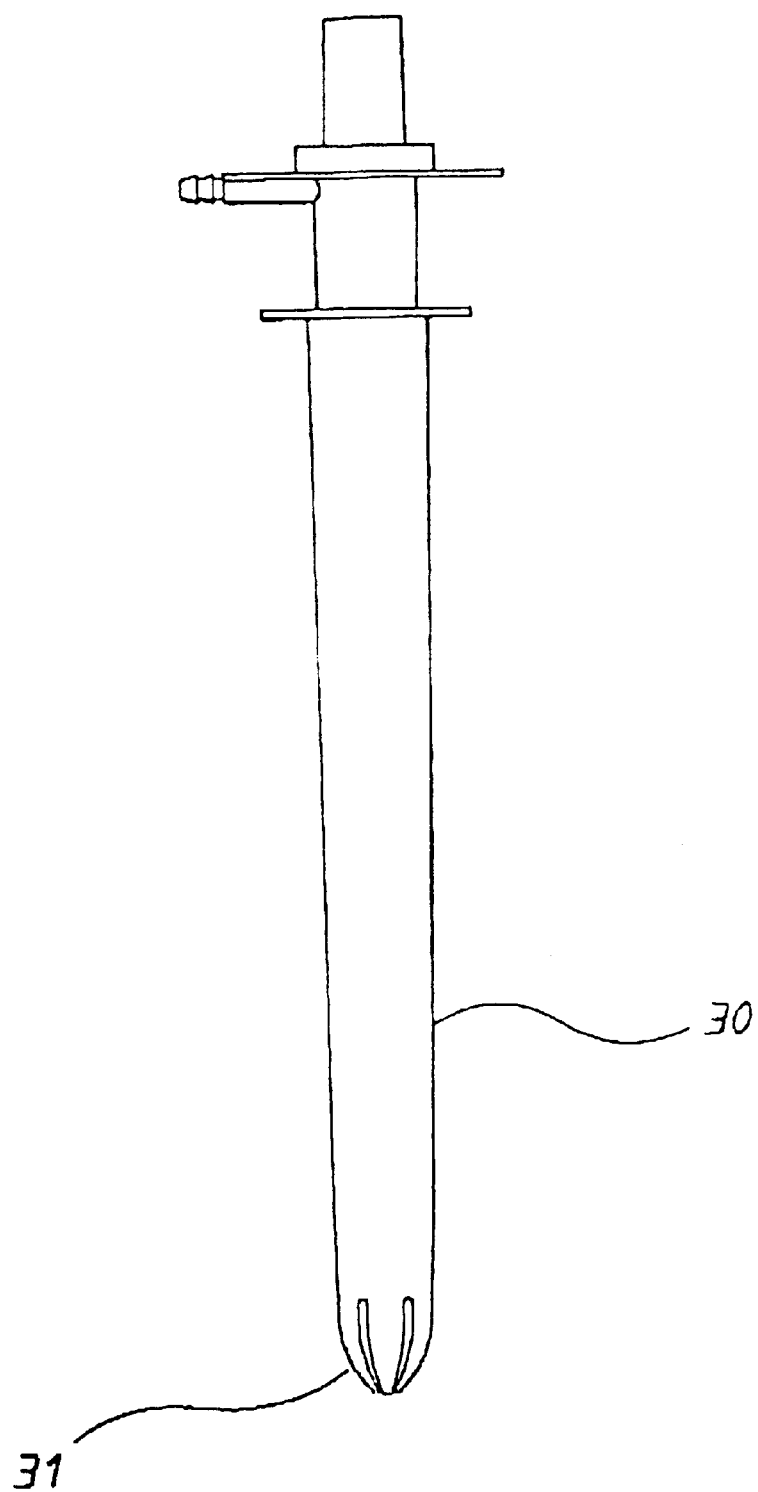
FIG. 5 shows a speculum and obturator assembly according to the invention in side elevation.
Figure 6:
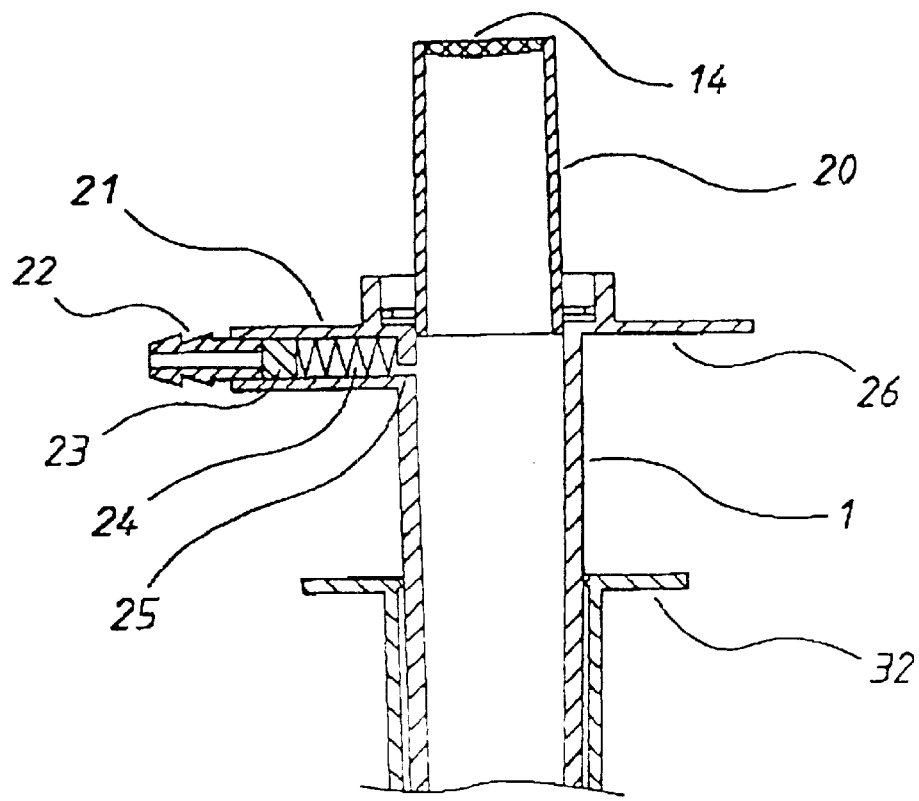
FIG. 6 shows the embodiment of FIG. 5 in cross-section.
Figure 6:
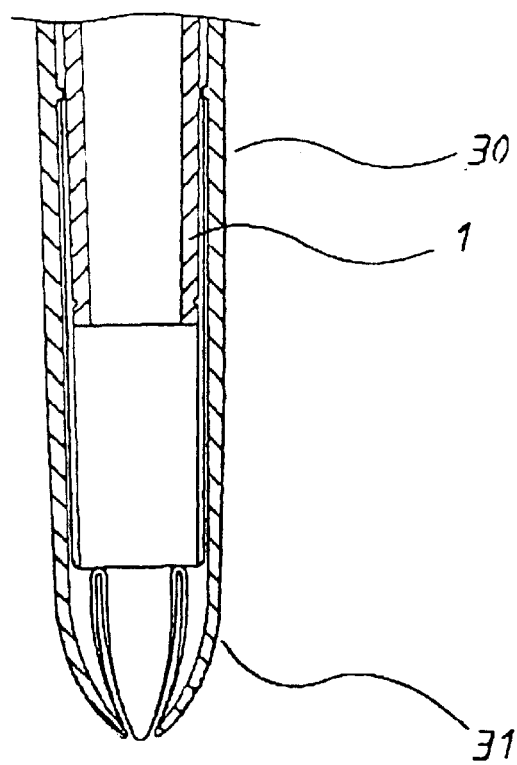
Figure 7:
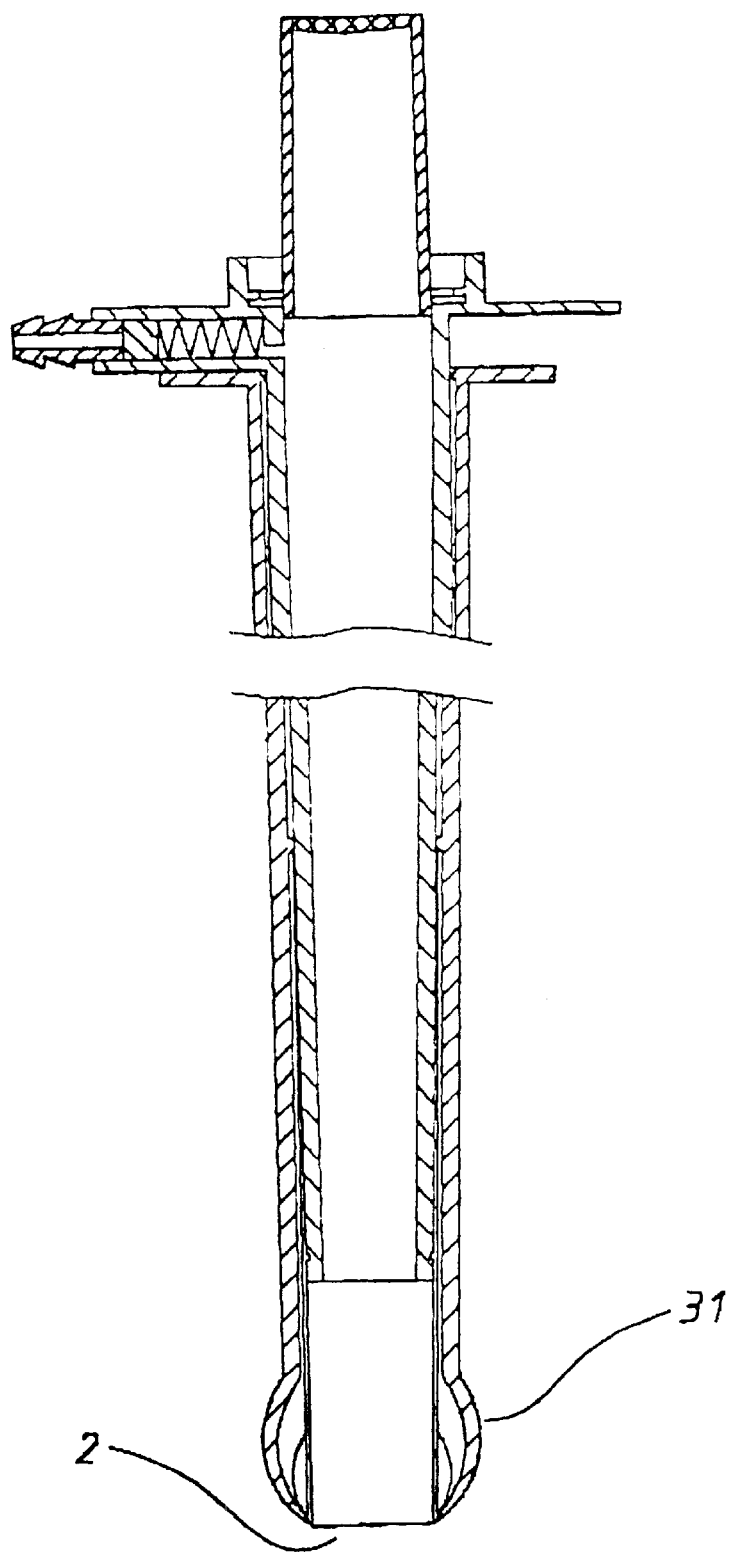
FIG. 7 shows the embodiment of FIG. 5 in cross-section and with the obturator retracted.
Figure 8:
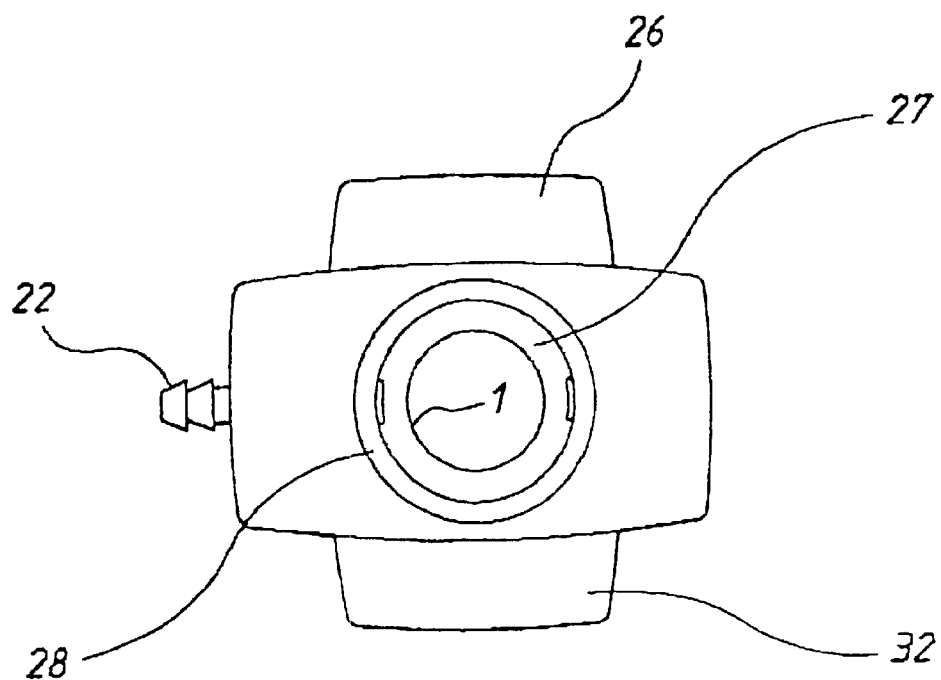
FIG. 8 shows the embodiment of FIG. 5 when viewed from the observation end.
Figure 9:
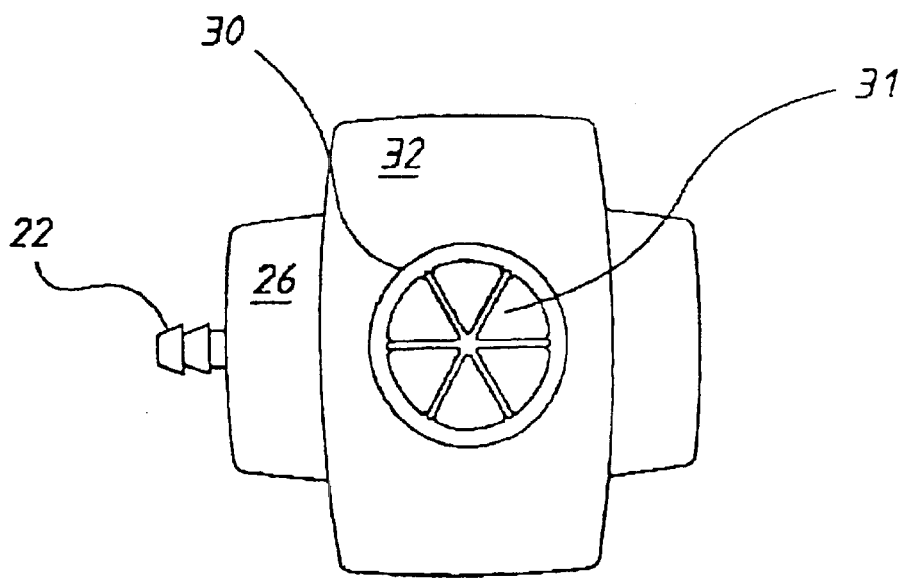
FIG. 9 shows the embodiment of FIG. 5 when viewed from the insertion end.

FIGS. 5–11 show a preferred embodiment of a speculum and obturator according to one aspect of the invention. In FIGS. 5–14 parts having a function corresponding with parts shown in FIG. 2 are identified with corresponding numerals. With reference to FIGS. 5–7, speculum I has an integral eyepiece 20 including integral window 14 which in this case may optionally be moulded in the form of a lens. Contamination prevention means 18 consists of a one-way valve assembly comprising a hollow side tube 21 formed integrally with disposable speculum 1 and adapted for connection with a reusable inflation bulb 10 by means of an externally ribbed spigot 22. The interior end of spigot 22 is sleeved by and sealed with side tube 21 and is adapted to provide a valve seat against which a sliding or rolling valve member 23 is urged by resilient means, for example a compression spring, 24. An opening 25 communicates between the interior of side tube 21 and the interior of speculum 1. When an inflation bulb 10 is operatively connected with spigot 22 and pumped, air pressure opens the valve and air flows from the bulb via opening 25 into speculum 1. Valve member 23 then closes against the valve seat by virtue of spring 24 preventing contamination of the insufflation bulb and tubing.

The embodiment of FIGS. 5–11 has a shield 26 into which is moulded a socket 27 defined by a circular flange 28 spaced radially outwardly of the circumferential observation end of speculum 1 whereby the speculum is adapted for coupling, for example by a bayonet connection, to a fibre optic head or light guide and light source (not illustrated in FIGS. 5–11).

The embodiments of FIGS. 5–11 is preferably provided with an external disposable obturator 30 which sleeves the exterior of speculum 1 and which is provided at the insertion end with a plurality of resiliently deformable petals or tangs 31 which are smoothly curved inwardly toward longitudinal axis of the speculum. Petals 31 are each curved inwardly along the edge thereof and rounded so as to avoid sharp edges. The obturator acts in a manner similar to obturator 13 during insertion. At its upper end obturator 30 is provided with a finger grip flange 32. After penetration the obturator is telescopically withdrawn with respect to the speculum resiliently deforming over speculum end 2 as is shown in FIG. 7 and permitting observation. Detents 33 engage formations 34 of the speculum to retain the obturator. Because obturator 30 does not need to be withdrawn via the interior of the speculum the risks of contamination by the obturator are eliminated. If the eyepiece remains closed there is no possibility of contamination.

Figure 12:
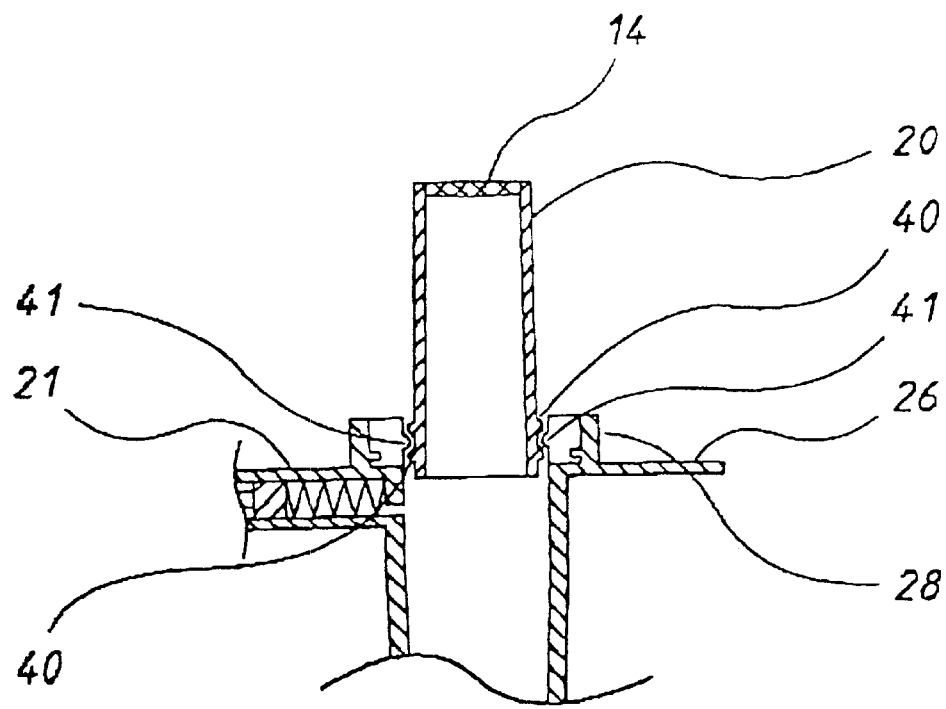
FIG. 12 shows an embodiment of an alternative eyepiece for use with the invention.

Although in the embodiment described in FIG. 5 disposable eyepiece 20 is integral with the speculum, eyepiece 20 may be a separate disposable part which is connectable with disposable speculum 1. Eyepiece 20 may simply be tapered on its external wall and be a push fit into the observation end of speculum 1. However because the device is pressurised in use, albeit lightly, it is preferred to have positive retention of disposable eyepiece 20. In FIG. 12 there is shown schematically an eyepiece with a fixed window 14 and which is adapted to be inserted into the observation end of speculum 1. Eyepiece 20 is provided with formations which resiliently interengage with those of the speculum. In the embodiment of FIG. 12 the eyepiece is provided with rings 40 extending circumferentially about the exterior of eyepiece 20 and which snap engage a ring 41 extending circumferentially on the interior of speculum 1 whereby to provide both retention and sealing between speculum 1 and eyepiece 20.

Figure 13:
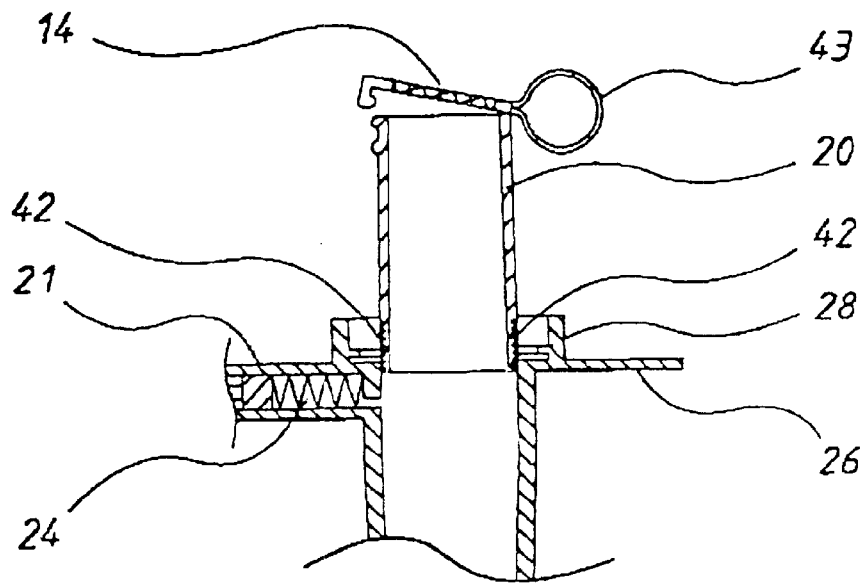
FIG. 13 shows another embodiment of an eyepiece for use with the invention.

In the embodiment of FIG. 13 the disposable eyepiece is in threaded engagement with the speculum by means of screw threads 42. In this embodiment window 14 is hinged, for example by means of a flexible integral hinge flap 43 although other hinging means may be employed. Window 14 may be sealed closed by a snap fastening for example resilient interengagable formations similar to those described for retaining eyepiece 20 in the embodiment of FIG. 12.

Figure 14:
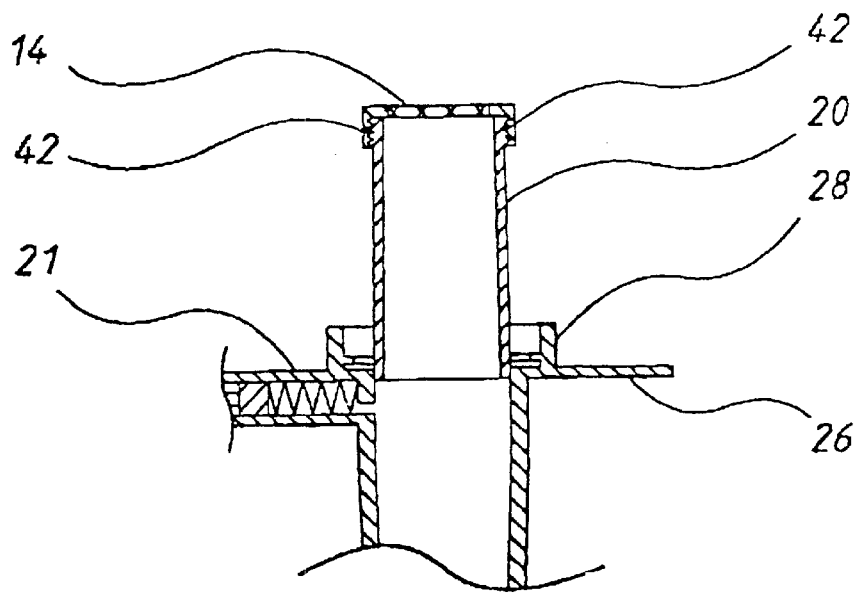
FIG. 14 shows another embodiment of an eyepiece for use with the invention.

In the embodiment of FIG. 14 there is shown a window 14 which is simply threadably engaged with an integral eyepiece 20. In other embodiments the eyepiece or the window may be retained by a bayonet fitting or other connection means.

Figure 15:
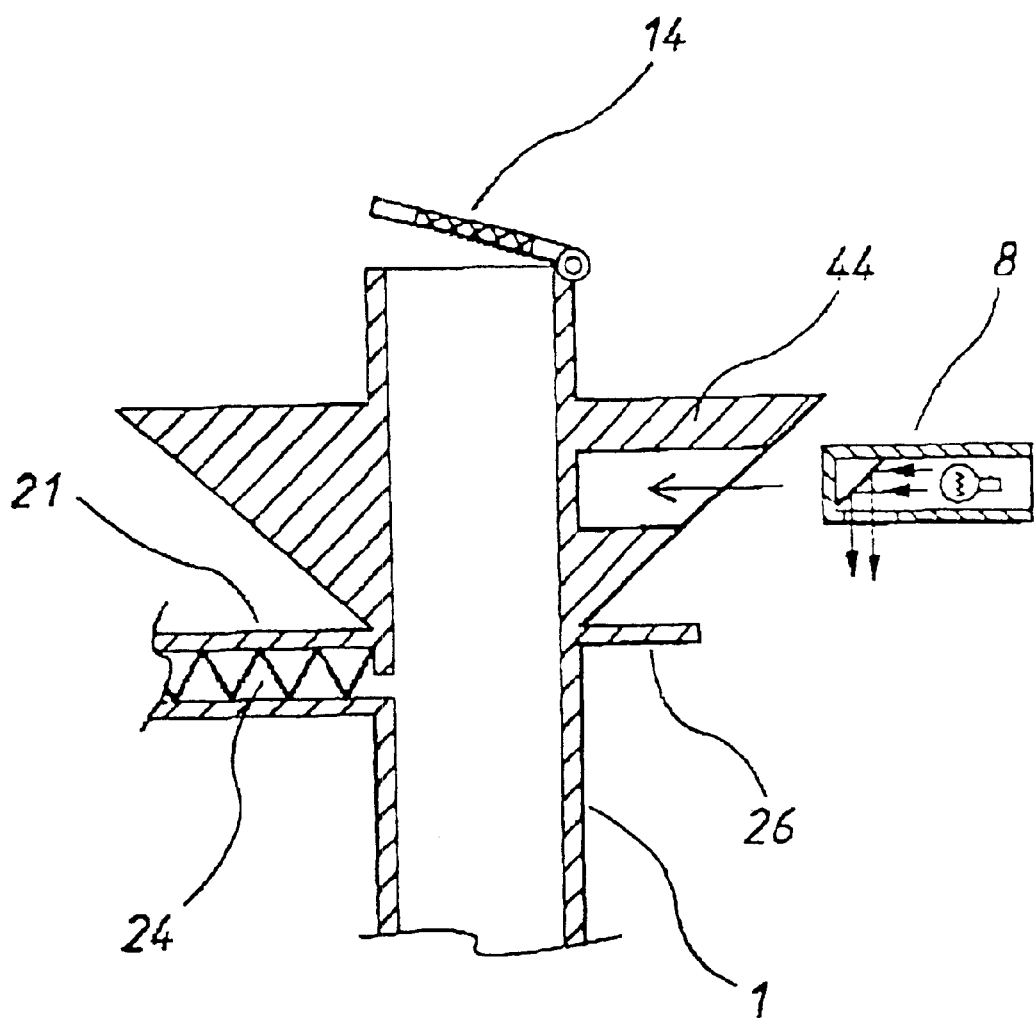
FIG. 15 shows schematically a disposable speculum having integral light coupling means.

In the embodiments of the invention described with reference to FIGS. 2–14 disposable speculum 1 is adapted for connection with a fibre optic head 5 whereby a light source 8 may be connected with the sigmoidoscope. Those embodiments differ from prior art in that the window is not a part of the coupling means but is disposable, and in that the interior of the sigmoidoscope (defined between the window and the interior of the speculum) does not communicate with any non-disposable part. In the embodiment of FIG. 15 there is shown schematically a speculum having integral optical coupling means which are disposed of with the speculum. In this embodiment only the illumination source in retained in the case in which a disposable inflation bulb is connected with the speculum, or an illumination source and inflation bulb are retained in the case in which the inflation bulb is connected via disposable contamination prevention means 18. Integral optical coupling means 44 is adapted to receive an attachable light source 8 which is plugged into a socket of the coupling. By suitable design of the light source, the light can be directed into the walls of the speculum and conducted for emission from the insertion end without the need for optical fibres. It may be desirable to coat parts of coupling 44 and/or other parts of the speculum with reflective coatings to facilitate guiding of the light from the light source. Optical coupling means 44 is desirably moulded integrally with speculum 1 or may be made from optical fibres and assembled permanently with the speculum for disposal rather than for disconnection and reuse.

Although inlet port 19 has been shown as communicating with the speculum interior by penetrating the wall of the speculum, it may penetrate via the eyepiece or via an integral optical coupling. It will be understood by those skilled in the art that features of one embodiment may be combined with those of another embodiment without departing from the scope of the invention herein disclosed.

Although in the embodiments illustrated the contamination prevention means 18 is a valve with a spring loaded valve member and valve seat, other kinds of non-return valve (eg Bunsen valves) may be substituted. Contamination prevention means 18 may be a filter selected to permit passage of an insufflation medium from the insufflation source to the bowel lumen and selected to prevent passage of contaminants or at least of contaminant carrying particles from the lumen to the insufflation source and may be in the form of a membrane, a plug, a hollow fibre filter, a molecular sieve or the like. Other means 18 might include a passage of sufficient tortuosity, an electrostatic precipitator, a cyclonic separating device or the like.

Figure 10:
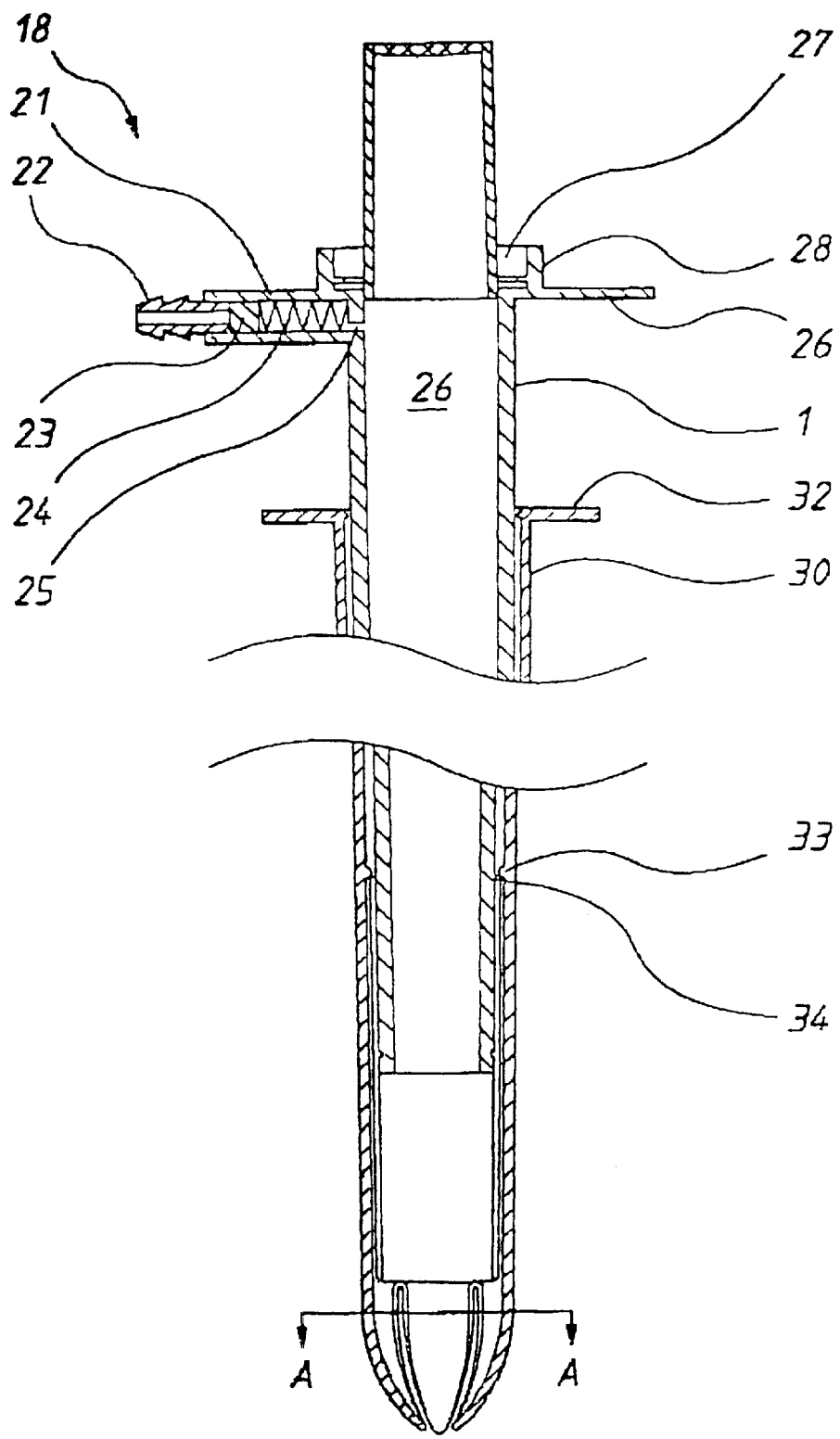
FIG. 10 shows the embodiment of FIG. 5 in more detail.
Figure 11:
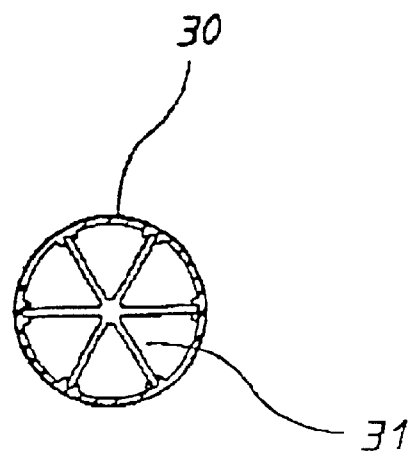
FIG. 11 shows a cross-section viewed on line A—A of FIG. 10.

The obturator shown in FIG. 10 may also be employed with speculum of the prior art. Although the obturator of FIG. 10 is external of the speculum, it will be understood that a similar design could be disposed internally of the speculum with radially outwardly biased tangs. If desired, light source 8 may also be made to be disposable.

Conceivably, insufflation means could be moulded in one piece with a disposable part, for example as a thin walled bulb moulded in communication with a sigmoidoscope disposable component and provided with a bulb inlet valve.

In other embodiments of the invention the bulb insufflator may be replaced with a disposable source of gas under pressure. The invention extends to include a method of sigmoidoscopy which includes the step of disposing of the insufflation means 10, 16 after each patient is examined. The invention also extends to include a method of sigmoidoscopy in which the insufflation means 10, 16 is not disposable but in which all parts of the sigmoidoscopy assembly and of the insufflation means and its connection which are exposed to contamination from the bowel are disposed of after one examination and prior to the next. The insufflation medium need not be air and may be another gas or liquid or vapour. Although the invention has been described with reference to specific examples it will be appreciated by those skilled in the art from the teaching hereof that the invention may be embodied in other forms without departing from the concepts herein taught.

What is claimed is:

1. A sigmoidoscope comprising at least one with means for insufflation of a body cavity with a medium via the medium being susceptible to contamination by a contaminant during use sigmoidoscope; said insufflation means and said sigmoidoscope being connected, or adapted for connection, one to the other; said sigmoidoscope and/or said insufflation means being provided with disposable contamination prevention means, or being so formed and arranged, that any non-disposable part of said sigmoidoscope and said insufflation means is not exposed to any contaminated medium during use of said sigmoidoscope, wherein the contamination prevention means is a filter.

2. A sigmoidoscope comprising at least one disposable part, in combination with means for insufflation of a body cavity with a medium via the sigmoidoscope; the medium being susceptible to contamination by a contaminant during use of said sigmoidoscope; said insufflation means and said sigmoidoscope being connected, or adapted for connection, one to the other; said sigmoidoscope and/or said insufflation means being provided with disposable contamination prevention means, or being so formed and arranged, that any non-disposable part of said sigmoidoscope and said insufflation means is not exposed to any contaminated medium during use of said sigmoidoscope, wherein the contamination prevention means is a precipitator.

3. A sigmoidoscope comprising at least one disposable part, in combination with means for insufflation of a body cavity with a medium via the sigmoidoscope; the medium being susceptible to contamination by a contaminant during use of said sigmoidoscope; said insufflation means and said sigmoidoscope being connected, or adapted for connection, one to the other; said sigmoidoscope and/or said insufflation means being provided with disposable contamination prevention means, or being so formed and arranged, that any non-disposable part of said sigmoidoscope and said insufflation means is not exposed to any contaminated medium during use of said sigmoidoscope, wherein the contamination prevention means is a tortuous passageway.

4. A sigmoidoscope comprising at least one disposable part, in combination with means for insufflation of a body cavity with a medium via the sigmoidoscope; the medium being susceptible to contamination by a contaminant during use of said sigmoidoscope; said insufflation means and said sigmoidoscope being connected, or adapted for connection, one to the other; said sigmoidoscope and/or said insufflation means being provided with disposable contamination prevention means, or being so formed and arranged, that any non-disposable part of said sigmoidoscope and said insufflation means is not exposed to any contaminated medium during use of said sigmoidoscope, wherein the contamination prevention means is a combination of two or more members selected from the group consisting of non-return valves, filters, precipitators and tortuous passageways.

5. A sigmoidoscope comprising at least one disposable part, in combination with reusable means for insufflation of a body cavity with a medium via the sigmoidoscope; the medium being susceptible to contamination by a contaminant during use of said sigmoidoscope; said insufflation means and said sigmoidoscope being connected, or adapted for connection, one to the other; said sigmoidoscope and/or said insufflation means being provided with disposable contamination prevention means, or being so formed and arranged, that any non-disposable part of said sigmoidoscope and said insufflation means is not exposed to any contaminated medium during use of said sigmoidoscope, said sigmoidoscope including a disposable speculum including an insertion end, an interior and an observation end, a disposable window at or adjacent to said observation end, means for optically coupling a light source which is external of said speculum with said sigmoidoscope so that light may be guided from the source for emission from said insertion end of said speculum during observation, and said reusable insufflation means communicating with said interior of said speculum, said sigmoidoscope being characterized in that said insufflation means are in communication with said interior of said speculum via said contamination prevention means which permits said interior of said speculum to be pressurized while preventing exposure of said insufflation means to contaminated insufflation medium, said sigmoidoscope including an eyepiece, said eyepiece associated with an inlet, wherein said insufflation means communicates with said interior of said disposable speculum via said inlet associated with said eyepiece.

6. Apparatus according to claim 5 wherein said disposable part is said eyepiece.

7. A sigmoidoscope comprising at least one disposable part, in combination with means for insufflation of a body cavity with a medium via the sigmoidoscope; the medium being susceptible to contamination by a contaminant during use of said sigmoidoscope; said insufflation means and said sigmoidoscope being connected, or adapted for connection, one to the other; said sigmoidoscope and/or said insufflation means being provided with disposable contamination prevention means, or being so formed and arranged, that any non-disposable part of said sigmoidoscope and said insufflation means is not exposed to any contaminated medium during use of said sigmoidoscope, wherein the contamination prevention means is a disposable non-return valve.

8. A sigmoidoscope comprising at least one disposable part, in combination with means for insufflation of a body cavity with a medium via the sigmoidoscope; the medium being susceptible to contamination by a contaminant during use of said sigmoidoscope; said insufflation means and said sigmoidoscope being connected, or adapted for connection, one to the other; said sigmoidoscope and/or said insufflation means being provided with disposable contamination prevention means, or being so formed and arranged, that any non-disposable part of said sigmoidoscope and said insufflation means is not exposed to any contaminated medium during use of said sigmoidoscope, said sigmoidoscope including an interior portion and an exterior portion and said sigmoidoscope including a first inlet port for operatively connecting said non-disposable insufflation means external of said sigmoidoscope with said interior portion of said sigmoidoscope, whereby, in use said inlet port permits pressurization of said interior portion, and wherein said disposable contamination prevention means is adapted to prevent a contaminated insufflation medium from passing from said interior portion of said sigmoidoscope inlet port to said exterior portion of said sigmoidoscope, wherein the contamination prevention means is a filter.

9. A sigmoidoscope comprising at least one disposable part, in combination with means for insufflation of a body cavity with a medium via the sigmoidoscope; the medium being susceptible to contamination by a contaminant during use of said sigmoidoscope; said insufflation means and said sigmoidoscope being connected, or adapted for connection, one to the other; said sigmoidoscope and/or said insufflation means being provided with disposable contamination prevention means, or being so formed and arranged, that any non-disposable part of said sigmoidoscope and said insufflation means is not exposed to any contaminated medium during use of said sigmoidoscope, said sigmoidoscope including an interior portion and an exterior portion and said sigmoidoscope including a first inlet port for operatively connecting said non-disposable insufflation means external of said sigmoidoscope with said interior portion of said sigmoidoscope, whereby, in use said inlet port permits pressurization of said interior portion, and wherein said disposable contamination prevention means is adapted to prevent a contaminated insufflation medium from passing from said interior portion of said sigmoidoscope inlet port to said exterior portion of said sigmoidoscope, wherein the contamination prevention means is a tortuous passage.

10. A sigmoidoscope comprising at least one disposable part, in combination with means for insufflation of a body cavity with a medium via the sigmoidoscope; the medium being susceptible to contamination by a contaminant during use of said sigmoidoscope; said insufflation means and said sigmoidoscope being connected, or adapted for connection, one to the other; said sigmoidoscope and/or said insufflation means being provided with disposable contamination prevention means, or being so formed and arranged, that any non-disposable part of said sigmoidoscope and said insufflation means is not exposed to any contaminated medium during use of said sigmoidoscope, said sigmoidoscope including an interior portion and an exterior portion and said sigmoidoscope including a first inlet port for operatively connecting said non-disposable insufflation means external of said sigmoidoscope with said interior portion of said sigmoidoscope, whereby, in use said inlet port permits pressurization of said interior portion, and wherein said disposable contamination prevention means is adapted to prevent a contaminated insufflation medium from passing from said interior portion of said sigmoidoscope inlet port to said exterior portion of said sigmoidoscope, said sigmoidoscope including a hollow cylindrical obturator, said obturator including an insertion end and a plurality of resiliently deformable petals, said petals located at said insertion end, and wherein said obturator is disposed in telescopic relationship with said speculum.

11. Apparatus according to claim 10 wherein said speculum includes a cylindrical axis, said obturator is external of said speculum, and wherein said petals located on said obturator are formed inwardly towards said cylindrical axis of said speculum.

12. Apparatus according to claim 11 wherein the petals are resiliently biased.

13. A sigmoidoscope comprising at least one disposable part, in combination with reusable means for insufflation of a body cavity with a medium via the sigmoidoscope; the medium being susceptible to contamination by a contaminant during use of said sigmoidoscope; said insufflation means and said sigmoidoscope being connected, or adapted for connection, one to the other; said sigmoidoscope and/or said insufflation means being provided with disposable contamination prevention means, or being so formed and arranged, that any non-disposable part of said sigmoidoscope and said insufflation means is not exposed to any contaminated medium during use of said sigmoidoscope, said disposable part of said sigmoidoscope being adapted for connection to said reusable insufflation means, said disposable part being provided with said contamination prevention means for preventing contaminated insufflation medium from contact with said insufflation means, wherein said contamination prevention means is a filter.

14. A sigmoidoscope comprising at least one disposable part, in combination with means for insufflation of a body cavity with a medium via the sigmoidoscope; the medium being susceptible to contamination by a contaminant during use of said sigmoidoscope; said insufflation means and said sigmoidoscope being connected, or adapted for connection, one to the other; said sigmoidoscope and/or said insufflation means being provided with disposable contamination prevention means, or being so formed and arranged, that any non-disposable part of said sigmoidoscope and said insufflation means is not exposed to any contaminated medium during use of said sigmoidoscope, said sigmoidoscope including an obturator and a speculum, wherein said obturator is disposed coaxially with, and externally of, said speculum.

15. Apparatus according to claim 14, wherein said obturator includes a leading end and defines a plurality of petals, and said speculum has an axis, and wherein said petals are located at said leading end of said obturator and said petals curving inwardly to said axis of said speculum.

16. Apparatus according to claim 14, wherein said obturator is further comprised of a hollow plastic tube, said tube including good light transmission properties.

17. Apparatus according to claim 14 wherein said apparatus is made of plastic.

18. A sigmoidoscope comprising at least one disposable part, in combination with means for insufflation of a body cavity with a medium via the sigmoidoscope; the medium being susceptible to contamination by a contaminant during use of said sigmoidoscope; said insufflation means and said sigmoidoscope being connected, or adapted for connection, one to the other; said sigmoidoscope and/or said insufflation means being provided with disposable contamination prevention means, or being so formed and arranged, that any non-disposable part of said sigmoidoscope and said insufflation means is not exposed to any contaminated medium during use of said sigmoidoscope, said sigmoidoscope including an obturator and a disposable speculum, wherein said obturator includes a hollow tube, said hollow tube including a tubular axis and first and second ends, and wherein said first end of said hollow tube includes a flange and said second end of said hollow tube includes a plurality of petals curving inwardly towards said tubular axis, and wherein said speculum includes an external surface and said hollow tube is adapted to sleeve said external surface of said disposable speculum.

\* \* \* \* \*

UNITED STATES PATENT AND TRADEMARK OFFICE
CERTIFICATE OF CORRECTION

PATENT NO. : 6,350,233 B1
DATED : February 26, 2002
INVENTOR(S) : David Z. Lubowski It is certified that error appears in the above-identified patent and that said Letters Patent is hereby corrected as shown below:

Column 10,
Line 13, after "at least one", insert -- disposable part, in combination --.
Line 14, after "medium via", insert -- the sigmoidoscope; --.
Line 16, after "during use", insert -- of said --.

Column 12,
Line 48, delete "said" and insert -- a --.

Signed and Sealed this

Eighteenth Day of October, 2005

JON W. DUDAS
*Director of the United States Patent and Trademark Office*